United States Patent
Samuilov

(10) Patent No.: US 10,247,689 B2
(45) Date of Patent: Apr. 2, 2019

(54) LOW CONCENTRATION AMMONIA NANOSENSOR

(71) Applicant: The Research Foundation for The State University of New York, Albany, NY (US)

(72) Inventor: Vladimir Samuilov, Sound Beach, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 77 days.

(21) Appl. No.: 15/371,624

(22) Filed: Dec. 7, 2016

(65) Prior Publication Data

US 2017/0082565 A1    Mar. 23, 2017

Related U.S. Application Data

(63) Continuation of application No. 14/031,322, filed on Sep. 19, 2013, now Pat. No. 9,541,517, which is a
(Continued)

(51) Int. Cl.
*G01N 27/30* (2006.01)
*G01N 27/12* (2006.01)
(Continued)

(52) U.S. Cl.
CPC ............ *G01N 27/126* (2013.01); *B82Y 15/00* (2013.01); *G01N 27/127* (2013.01); *G01N 27/30* (2013.01); *G01N 33/0054* (2013.01); *B82Y 30/00* (2013.01)

(58) Field of Classification Search
CPC .... G01N 27/126; G01N 27/30; G01N 27/127; G01N 33/0054; B82Y 15/00; B82Y 30/00
See application file for complete search history.

(56) References Cited

U.S. PATENT DOCUMENTS 5,069,220 A    12/1991  Casparie et al.
5,869,007 A    2/1999   Jang
(Continued)

FOREIGN PATENT DOCUMENTS

RU    2 038 590 C1    6/1995
RU    2 132 551 C1    6/1999
(Continued)

OTHER PUBLICATIONS

E. Lafuente, et al. "The influence of single-walled carbon nanotube functionalization on the electronic properties of their polyaniline composites" Carbon 46(14): p. 1909-1917, Nov. 2008.*
(Continued)

*Primary Examiner* — J. Christopher Ball
(74) *Attorney, Agent, or Firm* — Scully, Scott, Murphy & Presser, P.C.

(57) ABSTRACT

An electrochemical sensor for sensing a gaseous analyte includes a substrate having at least two electrodes disposed thereon, and a carbon nanotube-polyaniline (CNT/PANI) film disposed on the substrate and in contact with at least two electrodes. The CNT/PANI film includes carbon nanotubes coated with a thin layer of polyaniline. The thickness of the polyaniline coating is such that electron transport can occur along and/or between the carbon nanotubes.

23 Claims, 4 Drawing Sheets

Related U.S. Application Data continuation of application No. PCT/US2012/055134, filed on Sep. 13, 2012.

(60) Provisional application No. 61/535,645, filed on Sep. 16, 2011.

(51) Int. Cl.
*B82Y 15/00* (2011.01)
*G01N 33/00* (2006.01)
*B82Y 30/00* (2011.01)

(56) References Cited

U.S. PATENT DOCUMENTS

| | | | |
|---|---|---|---|
| 6,156,346 | A | 12/2000 | Chen et al. |
| 7,374,703 | B2 | 5/2008 | Epstein et al. |
| 2005/0214806 | A1 | 9/2005 | Braun et al. |
| 2007/0102654 | A1 | 5/2007 | Schoo |
| 2007/0272901 | A1 | 11/2007 | Gouma |
| 2008/0077037 | A1 | 3/2008 | Gouma et al. |
| 2008/0093226 | A1 | 4/2008 | Briman et al. |
| 2009/0278556 | A1 | 11/2009 | Man et al. |
| 2010/0089772 | A1 | 4/2010 | Deshusses et al. |
| 2012/0237968 | A1 | 9/2012 | Rigas |
| 2014/0021067 | A1 | 1/2014 | Samuilov |

FOREIGN PATENT DOCUMENTS

| | | |
|---|---|---|
| RU | 2 213 393 C2 | 9/2003 |
| RU | 2 386 191 C1 | 4/2010 |
| WO | WO 20081/153593 A1 | 12/2008 |

OTHER PUBLICATIONS

Gong J. et al., "Ultrasensitive NH3 Gas Sensor from Polyaniline Nanograin Enchased TiO2 Fibers", J. Phys. Chem. C 114:9970-9974 (2010).
Gouma P. et al., "Nanosensor and Breath Analyzer for Ammonia Detection in Exhaled Human Breath", Sensors Journal, IEEE 10(1):49-53 (Dec. 8, 2009).
He L. et al., "Gas Sensors for Ammonia Detection Based on Polyaniline-Coated Multi-Wall Carbon Nanotubes", Materials Science and Engineering B 163:76-81 (2009).
Kearney D.J. et al., "Breath Ammonia Measurement in Helicobacter Pylori Infection", Digestive Diseases and Sciences 47(11):2523-2530 (Nov. 2002).
Ksenevich V.K. et al., "Charge Carrier Transport Properties in Single-Walled Carbon Nanotube Fibers", Acta Physica Polonica A 113(3)1039-1042 (2008).
Ksenevich V.K. et al., "Localization and Nonlinear Transport in Single Walled Carbon Nanotube Fibers", Journal of Applied Physics 104:073724-1-073724-7 (2008).
Ksenevich V.K. et al., "Magnetotransport in Mesoscopic Carbon Networks in the Vicinity of Metal-Insulator Transition", Physica E 17:389-390 (2003).
Liu H. et al., "Polymeric Nanowire Chemical Sensor", Nano Letters 4(4):671-675 (2004).
Lu Q. et al., "Temperature Dependent Resistance and Magnetoresistance of Single Wall Carbon Nanotubes Mounted on Silica Fiber Surfaces", Chapter 8, pp. 185-196 (2011).
Samuilov V.A. et al., "Magnetotransport in Mesoscopic Carbon Networks", Physica B 294-295:319-323 (2001).
Seliuta D. et al., "Terahertz Sensing With Carbon Nanotube Layers Coated on Silica Fibers: Carrier Transport Versus Nanoantenna Effects", Applied Physics Letters 97:073116-1-073116-3 (2010).
Srivastava S. et al., "Characterization of Gas Sensing Behaviour of Multi Walled Carbon Nanotube Polyaniline Composite Films", International Journal of Hydrogen Energy 34:8444-8450 (2009).
Tai H. et al., "In-Situ Self-Assembled Polyaniline/Carbon Nanotubes Nanofiber Thin Films for Ammonia Gas Sensors", 5th International Symposium on Advanced Optical Manufacturing and Testing Technologies: Optoelectronic Materials and Devices for Detector, Imager, Display, and Energy Conversion Technology 7658:76582T-1-76582T-6 (2010).
Wang G., "Organic/Inorganic Nanocomposite Materials by Electrospinning and Their Properties", A Dissertation, Stony Brook University (184 pages) (Dec. 2007).
Wang G. et al., "Conducting MWNT/Poly(Vinyl Acetate) Composite Nanofibres by Electrospinning", Nanotechnology 17:5829-5835 (2006).
Zhang T. et al., "Humidity-Independent Gas Nanosensor", Supplementary Information (1 page).
Zhang T. et al., "A Gas Nanosensor Unaffected by Humidity", Nanotechnology 20:255501 (5 pages) (2009).
Zhang T. et al., "Electrochemically Functionalized Single-Walled Carbon Nanotube Gas Sensor", Electroanalysis 18:1153-1158 (2006).
International Search Report and Written Opinion dated Dec. 13, 2012 received from International Application No. PCT/US2012/055134.
U.S. Office Action dated Aug. 18, 2016 received in U.S. Appl. No. 14/031,322.
U.S. Office Action dated Feb. 26, 2016 received in U.S. Appl. No. 14/031,322.
U.S. Office Action dated Mar. 15, 2013 received in U.S. Appl. No. 13/420,384.

* cited by examiner

LOW CONCENTRATION AMMONIA NANOSENSOR

CROSS REFERENCE TO RELATED APPLICATIONS

The present application is a continuation of a co-pending application having U.S. Ser. No. 14/031,322, filed on Sep. 19, 2013, which is a continuation of PCT Application N. PCT/US2012/055134, filed Sep. 13, 2012 and based upon and claiming the benefit of priority from U.S. Provisional Application No. 61/535,645, filed Sep. 16, 2011, the entire contents of all of which are incorporated herein by reference.

BACKGROUND OF THE INVENTION

Technical Field

The present invention generally relates to sensors and methods for sensing a gaseous analyte.

Background Information

Gas detection instruments or sensors have a wide range of applications, including industrial health and safety, environmental monitoring, and process control. Sensors are used in a variety of fields, including chemical and petroleum refining, rocket fuel production, fuel cell manufacturing, semiconductor processing, and biomedical applications. For example, nanoscale sensors can be used to detect certain gaseous analytes in a sample, such as human exhaled breath. The presence and concentration of particular analytes may be used to diagnose various diseases.

Nanoscale sensors comprise nanomaterials such as carbon nanotubes (CNTs). Nanomaterials can exhibit sensitivity to gases. For example, in view of their unique electrical, thermal, and mechanical properties, CNTs can be used to make gas sensors. Other nanomaterials have also shown promise for use as gas sensors.

The sensing mechanism of nanomaterial-based gas sensors depends either upon charge transfer between the nanostructure building blocks or, due to adsorption of charged or polar molecules of the gases on the surfaces of the nanostructure building blocks. An electron donation or withdrawal due to adsorption of the gas analytes changes the conductivity of the nanomaterials. Nanomaterial-based sensors, therefore, using low-power microelectronics technology, convert chemical information into an electrical signal, leading to the formation of miniaturized sensor devices.

CNTs and other nanostructures, such as nanowires and nanodots, have been demonstrated as appealing sensing materials for developing advanced chemical gas sensors. Based on the mechanism of charge transfer, gas adsorption (for example, nitrogen dioxide ($NO_2$), ammonia ($NH_2$), and oxygen ($O_2$)) can cause significant electrical transport property changes in the CNTs and nanowires and nanodots, which can be beneficial for sensing applications.

However, gas sensors based on bare nanomaterials, such as pristine CNTs, have limitations, including low sensitivity (due, for example, to low absorption capacity), and a lack of selectivity to analytes for which they have low adsorption energy or low affinity. This less-than-ideal sensitivity and selectivity has limited the use of nanomaterial-based gas sensors in practical applications. Efforts have been made to improve gas sensitivity and selectivity of CNTs by functionalizing the CNTs with analyte-specific materials. However, functionalization of the sensors can require long fabrication time and complicated fabrication steps, which can make the process complex and costly.

Conducting polymers represent one type of sensitive material that has been investigated for CNT functionalization. For example, polyaniline (PANT) has been used as a sensing material for a variety of toxic gases such as carbon monoxide, nitrogen dioxide, and ammonia. PANI exhibits p-type semiconductor characteristics, so electron-supplying gases such as ammonia reduce the charge-carrier concentration and decrease the conductivity of the polymer. However, CNT functionalization can involve complex fabrication processes, and resulting functionalized CNTs can lack the desired properties for sensing applications.

A need exists for improved CNT gas sensors and methods that do not require a complex fabrication process or high operating temperatures, and that have the desired properties for sensing applications, including, for example, low resistivity and high resolution, specifically at low analyte concentrations.

SUMMARY OF THE INVENTION

Briefly, the present invention satisfies the need for gas sensors and methods that do not require a complex fabrication process or high operating temperatures, and that have desired properties for sensing applications. The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

Certain embodiments of the presently-disclosed gas sensors and methods for producing gas sensors have several features, no single one of which is solely responsible for their desirable attributes. Without limiting the scope of these gas sensors and methods as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. These advantages may include, without limitation, simplified and efficient methods of fabricating electrochemical gas sensors having good sensing properties, such as high sensitivity, low detection limits, fast response and recovery times, good reproducibility, good selectivity in the detection of gases, and long term stability.

The present invention provides, in a first aspect, an electrochemical sensor for sensing a gaseous analyte. The sensor includes a substrate which has two or more electrodes disposed thereon, and a carbon nanotube-polyaniline film disposed on the substrate and in contact with at least two electrodes. The carbon nanotube-polyaniline film includes carbon nanotubes coated with a thin layer of polyaniline having a thickness such that electron transport can occur along and/or between the carbon nanotubes.

The present invention provides, in a second aspect, a method of making an electrochemical sensor for sensing a gaseous analyte. The method includes preparing a solution of polyaniline and camphorsulfonic acid in chloroform, preparing a solution of octadecylamine functionalized carbon nanotubes in chloroform, mixing the two solutions, and depositing the mixed solution on a substrate which has at least two electrodes disposed over it, to form a carbon nanotube/polyaniline film on the substrate, such that the film is in contact with at least two electrodes. The film comprises carbon nanotubes coated with a thin layer of polyaniline of thickness such that electron transport can occur along and/or between the carbon nanotubes. The film can be formed by spin-coating the mixed CNT/PANI solution.

These and other features and advantages of this invention will become apparent from the following detailed description of the various aspects of the invention taken in conjunction with the appended claims and the accompanying drawings.

DETAILED DESCRIPTION OF THE INVENTION

Figure 1:
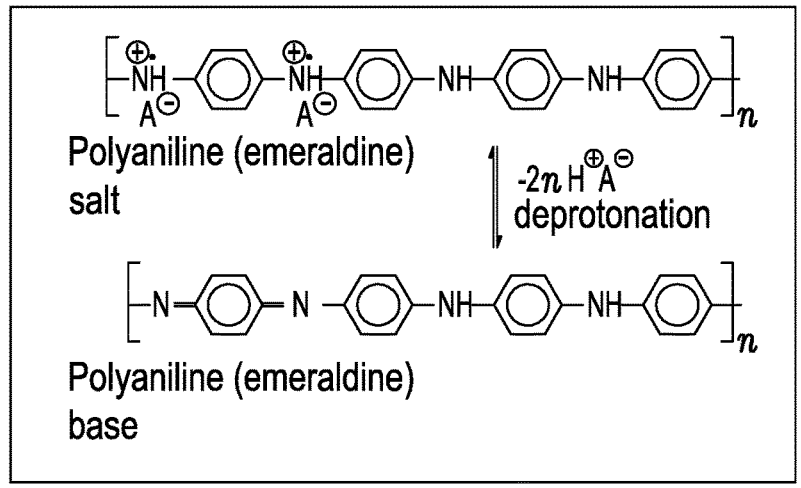
FIG. 1 shows a mechanism for chemical sensing using polyaniline.

The present invention is generally directed to electrochemical sensors for sensing a gaseous analyte, and to methods of making electrochemical sensor for sensing a gaseous analyte.

Although this invention is susceptible to embodiment in many different forms, certain embodiments of the invention are shown. It should be understood, however, that the present disclosure is to be considered as an exemplification of the principles of this invention and is not intended to limit the invention to the embodiments illustrated.

The presently-disclosed electrochemical sensors, in one aspect, provide a device for detecting or sensing a particular gas or gases (e.g., hydrogen, hydrogen sulfide, ammonia, nitrogen dioxide, water vapor, oxygen, or methane) in a gaseous environment. In various embodiments, the sensors comprise carbon nanostructures, which are coated with a material which is used to functionalize the nanostructure.

In some embodiments, the carbon nanostructures are carbon nanowires and/or carbon nanotubes (CNTs), for example, single-walled nanotubes (SWNTs) or multi-walled nanotubes (MWNTs), although this list is non-limiting and other carbon nanostructures may also be used.

In some embodiments, the material used to functionalize the nanostructures is chosen based on the gaseous analyte(s) to be detected. For example, in some embodiments, the material comprises palladium (used for detecting, e.g., hydrogen), gold (used for detecting, e.g., hydrogen sulfide or mercury vapor), or a metal oxide (used for detecting, e.g., methane and/or ammonia). In certain embodiments, the material used to functionalize the nanostructures, such as CNTs, is a conductive polymer. For example, in some embodiments, the material comprises polyaniline (PANI) (used for detecting, e.g., ammonia, water vapor, and/or nitrogen dioxide).

In certain embodiments, the gas sensors and methods of the present invention use CNTs functionalized with polyaniline (PANI) doped with camphor-sulfonic acid (CSA). Such sensors may be used for detecting ammonia and/or nitrogen dioxide. PANI(CSA) is a typical sulfonated conducting polymer having tunable electronic properties coupled with good environmental and thermal stability. Gas sensors comprising CNTs (e.g., MWNTs) functionalized with PANI(CSA) exhibit humidity independence. Thus, these sensors can be used in a wide range of environments without the need to compensate for relative humidity, making the process of using the sensors simpler and less expensive.

The sensing mechanism of the sensors according to certain embodiments of the present invention is based on a charge interaction between the molecules of a specified gaseous analyte and the functionalized carbon nanostructures. Specifically, the electrical properties of the electrochemical sensor, particularly its resistance, change from a predetermined baseline value upon exposure to a gaseous environment containing the specified gaseous analyte as a result of the functionalized nanostructures accepting electrons from, or donating electrons to the molecules of a specific gaseous analyte to which the sensor is exposed, and to which the materials of the sensor are responsive.

In some embodiments, the change in a measured electrical property (e.g., resistance) is measured or quantified, directly or indirectly. For example, a change in resistance may manifest itself as a change in current flowing through a circuit including the sensor or a change in the voltage drop across the sensor. The change in current or voltage is then measured and calibrated to a quantifiable gas concentration value. The magnitude of the change in the measured parameter establishes the concentration of the specified gas present in the system when compared to a baseline or calibration value of the measured parameter. These types of sensors, also referred to as chemiresistive sensors, have desirable properties, such as high sensitivity, low detection limits, fast response and recovery times, good reproducibility, good selectivity in the detection of gases, and/or long term stability, such as within a range of temperatures.

In certain embodiments of the present invention, to assess the sensitivity of the sensors, measurements of the electrical signals are processed using direct current (DC) technique. The signals are digitized using standard acquisition boards, and the experimental information is processed using computers.

In certain embodiments of the present invention, the material used to functionalize the nanostructures is polyaniline. FIG. 1 shows a mechanism for chemical sensing using polyaniline. The nitrogen atoms along the PANI backbone make the material particularly sensitive to ammonia. Upon exposure to ammonia ($NH_3$), the emeraldine salt form of polyaniline is deprotonated to yield the less conducting emeraldine base form, and the ammonia forms more energetically favorable $NH_4^+$ ions. The change in resistivity from highly conducting to practically insulating is used to gauge the extent of chemical reactivity with the nitrogen bonding sites along the PANT backbone. Exposure of the PANI emeraldine salt to ammonia vapors produces this reversible de-doping effect, allowing sensors to be reused.

Figure 2:
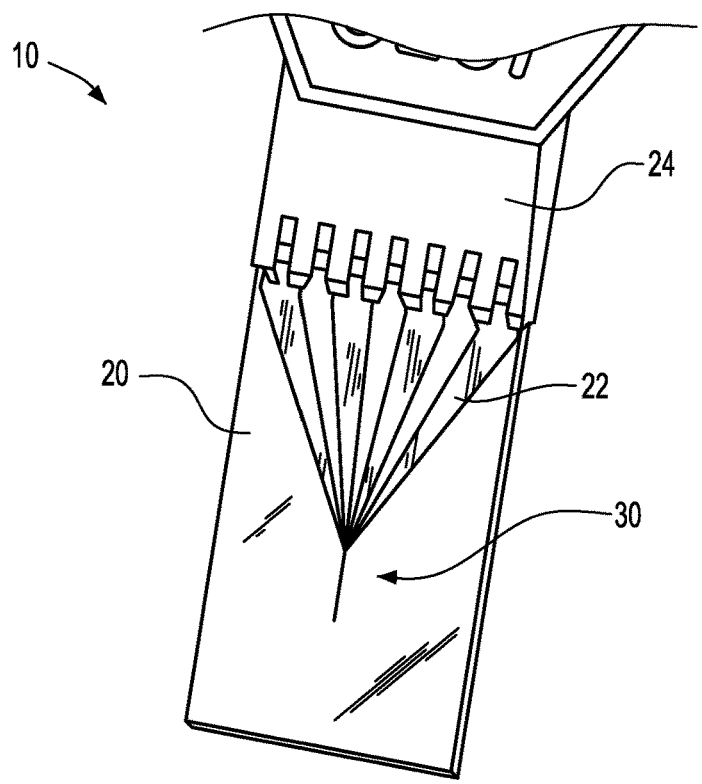
FIG. 2 is a top perspective view of one embodiment of an electrochemical sensor according to the present invention.

FIG. 2 is a top perspective view of one embodiment of an electrochemical sensor 10 according to the present invention. In the depicted embodiment, the gas sensor comprises a substrate 20, which is held by substrate holder 24. While the substrate 20 shown in the depicted embodiment is a 20×10 mm substrate, persons having ordinary skill in the art will readily understand that substrates of various alternative sizes are conducive to the instant invention. In embodiments of the present invention, the substrate 20 is a nonconductive or insulating material, such as glass. The substrate 20 has at least two conductive electrodes, formed or disposed thereon. In some embodiments, the electrodes extend from the contact pads 22 and lie in the active area 30 on substrate 20. Persons having ordinary skill in the art will understand that the size and shape of the active area 30 can vary depending on the number and dimension of the electrodes. For example, although not limiting, in certain embodiments the active area 30 tray be hundreds of microns or several millimeters in width and length, for example, from 1×1 mm to 8×8 mm, such as 4×4 mm.

In some embodiments, the electrodes may be formed on substrate 20 in a substantially parallel array, using any suitable method known in the art, for example, conventional photolithography, screen printing, electrodeposition, or standard sintering techniques. In certain embodiments, the electrodes may be formed of metals that do not oxidize easily, such as, for example, nickel, gold, platinum, palladium or other metals known in the art to be suitable for this application. Persons having ordinary skill in the art will understand that the electrodes may be of various widths and lengths. For example, although not limiting, in certain embodiments the electrodes may be in the range of 1 µm to 50 µm in width. The electrodes are separated by one or more gaps having a width which can vary. Although not limiting, in certain embodiments, the width of the gap(s) is in the range of several hundred nanometers to more than 100 µm. In one embodiment, the width of the gap between two electrodes is between 1 µm and 10 µm, such as, for example, 5 µm. While the substrate 20 comprises at least two electrodes, various embodiments of the present invention include more than two electrodes, such as three, four, five, six, or more electrodes. For example, although not pictures, in the depicted embodiment, the substrate 20 comprises four parallel planar platinum electrodes with 5 µm separation.

In certain embodiments of the present invention, a carbon nanotube-polyaniline (CNT/PANI) film (not visible in FIG. 2) is disposed on the substrate 20 such that it is in contact with at least two electrodes. The film may be disposed on the substrate 20 by any conventional methods known in the art, for example, by using the spin casting technique. In embodiments of the present invention using the spin casting technique, the resulting film thickness can be varied by changing the spin speed or the concentration of CNT/PANI in the solution to be spin-cast. PANI/CNT films are spin cast from chloroform at various speeds, for example, from 1000-3000 RPM at the system of electrodes.

In some embodiments, the CNT/PANI film comprises carbon nanotubes e.g., MWNTs or SWNTs) coated with a layer of polyaniline of thickness such that electron transport can occur along and/or between the coated carbon nanotubes.

In certain embodiments of the present invention, the average thickness of the polyaniline coating on the CNTs is less than the average diameter of the carbon nanotubes. In some embodiments, the polyaniline coating has an average thickness of less than 10 nm, or less than 9 nm, or less than 8 nm, or less than 7 nm, or less than 6 nm, or less than 5 nm, or less than 4 nm, or less than 3 nm, or less than 2 nm. In certain embodiments, the layer of polyaniline is transparent to electron tunneling, e.g., the energy barrier is low enough, and the thickness of the polyaniline layer separating two quantum wells (carbon nanotubes) is thin enough such that the probability of tunneling of a charge carrier (electron) in nonzero. This means, the PANI forms very thin gaps between nanotubes that are transparent to electron tunneling. When the layer of polyaniline is transparent to electron tunneling from CNT tube to tube, the conducting mechanism of the CNT/PANI film is due to electron transport along the tubes and electron tunneling through PANE gaps. "Tunneling thin" layers are discussed in Ostroumova et al., Semiconductors 33 (9), 1027-1029 September 1999, which is hereby incorporated by reference with respect to relative portions related to the subject matter of the present invention and all of its embodiments.

In certain embodiments of the present invention, the average diameter of the polyaniline-coated multiwall carbon nanotubes is greater than or equal to 10 nm and less than 50 nm. For example, in certain embodiments the average diameter of the polyaniline-coated carbon nanotubes is 10-45 nm, 10-30 nm, or 15-40 nm, or 20-40 nm.

In certain embodiments of the present invention, the CNT/PANI film has an average thickness between 40 and 400 nm. For example, in certain embodiments, the CNT/PANI film has an average thickness of 40-300 nm, or 40-250 nm, or 40-200 nm, or 40-100 nm, or 50-300 nm, or 50-250 nm, or 50-200 nm, or 50-100 nm, or 100-200 nm, or any intermediate range falling within one of the defined ranges (e.g., of thickness in rim having a range of any integer greater than 40 to any integer less than 300).

In some embodiments, gas sensors of the present invention are capable of sensing less than 400 ppm of a gaseous analyte, for example, less than 200 ppm or less than 100 ppm or less than 50 ppm or less 40 ppm or less than 30 ppm or less than 20 ppm or than 10 ppm or less than 1 ppm. In some embodiments, the gas sensors of the present invention are capable of sensing less than 500 ppb of a gaseous analyte, for example, less than 400 ppb or less than 300 ppb or less than 200 ppb or less than 175 ppb or less than 150 ppb or less than 125 ppb or less than 100 ppb or less than 75 ppb or less than 50 ppb or less than 25 ppb. In some embodiments, the gas sensors of the present invention are capable of sensing concentrations greater than or equal to 1 ppb of a gaseous analyte. According to certain embodiments, gas sensors of the present invention exhibit reversible sensor response toward gaseous analytes in the foregoing concentration ranges.

Figure 7:
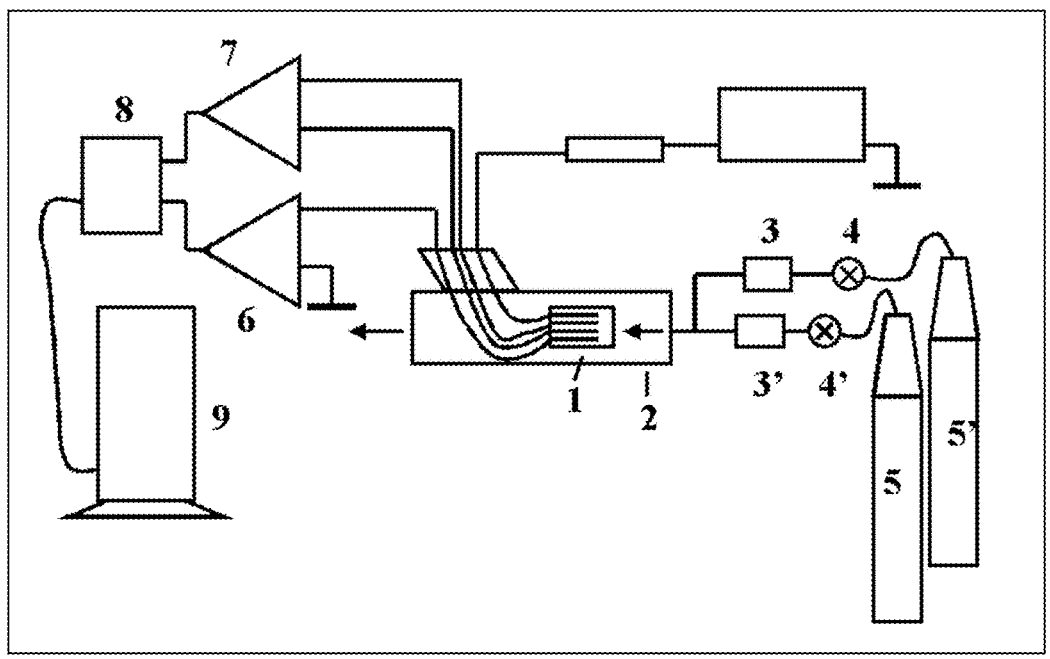
FIG. 7 depicts an example of an experimental setup for the quantitative measurements of gas sensors of the present invention.

FIG. 7 depicts an example of an experimental setup for the quantitative measurements of gas sensors of the present invention. In the depicted setup, the gas sensor 1 is located at the testing gas flow bench 2. Digital flow controllers 3 and 3' are connected to the pressure regulators 4 and 4', which are connected to gas cylinders 5 and 5'. The gas cylinders 5 and 5' may comprise, for example, $N_2$ as a carrier gas. The gases for testing can be different and/or diluted. Current pre-amplifier 6 and voltage preamplifier 7 are configured with A/D converter 8 and computer 9. The assembled configuration allows controllable flow rate of the testing gases from, for example, 1 to 100 sccm in the controllable flow rates from 10 to 1000 sccm.

The present invention also provides methods of detecting the presence of specific gaseous analytes in a gaseous environment (e.g., air), by using the gas sensors of the present invention. In certain embodiments, the methods include determining a baseline value of an electrical parameter (such as resistance) of the sensor, exposing the sensor to a gaseous environment that may include the specific gaseous analyte to be detected, and measuring any change in the electrical parameter value of the sensor after exposure to the gaseous environment. In one specific embodiment, the method is for detecting ammonia.

The present invention also provides methods of making an electrochemical sensor for sensing a gaseous analyte. In certain embodiments, the method comprises: (a) preparing a solution of polyaniline (PANI) and camphorsulfonic acid (CSA) in chloroform; (b) preparing a solution of octadecylamine (ODA) functionalized carbon nanotubes (CNTs, for example, MWNTs) in chloroform; (c) mixing the PANI/CSA solution and the ODA-functionalized CNT solution to make a CNT/PANI solution; and (d) depositing a CNT/PANI film on a substrate having at least two electrodes disposed thereon, such that the film is in contact with at least two electrodes. In certain embodiments, the CNT/PANI film comprises carbon nanotubes coated with a layer of polyaniline of thickness such that electron transport can occur along and/or between the carbon nanotubes, and said film is formed by any acceptable technique known in the art, for example, by spin-coating the CNT/PANI solution.

In certain embodiments of methods according to the present invention, the concentration of PANI in the PANI/CSA solution is equal to the concentration of CNTs in the ODA-functionalized CNT solution. In some embodiments, the CNT/PANI solution is a 50:50 mixture of PANI/CSA solution and ODA-functionalized CNT solution.

In certain embodiments of methods of making an electrochemical sensor for sensing a gaseous analyte according to the present invention, the gaseous analyte is ammonia. In some embodiments, the methods of the present invention produce sensors capable of sensing at least 1 ppb of ammonia.

In certain embodiments, the present invention provides sensors and methods having advantageous sensitivity, response and refraction times, linearity, bias stability, thermal stability, and/or regeneration rate of the gas sensors. For example, in some embodiments, the present invention provides sensors and methods having sensitivity to analytes at concentrations of 1 ppb. In some embodiments, the present invention provides sensors having a linear response to low analyte concentrations (e.g., to concentrations of, for example, less than 200 ppb, or less than 180 ppb, or less than 150 ppb, or less 120 ppb, or less than 100 ppb).

An embodiment of the above-described gas sensor was prepared for use in gas detection studies.

Samples Preparation.

Emeraldine base polyaniline (PANI-EB) with a molecular weight of 10and camphor-10 sulphonic acid B were purchased from Aldrich and used as received. PANI-EB and CSA were dissolved in chloroform at a molar ratio of 1:0.5 to completely protonate the PANI backbone to produce the emeraldine salt form (PANI-CSA). Solutions were stirred for 3 days and sonicated for 15 minutes prior to preparing PANI thin films. PANI/CNT films were made from PANI and CNT solutions in chloroform of equal concentrations (1 mg/ml). In order to reach this high solubility of CNT chloroform CNTs were functionalized with ODA. ODA functionalized CNTs were processed in the Lab, but can be purchased, for example, from M K Impex Corp. Division: MKnano.

PANI and CNT solutions are of equal concentration, a 50:50 blend solution was prepared by adding equal amounts. For our sensors we used 50:50 solution to compare with 100% PANI-doped by CSA.

Thin films were prepared using the spin casting technique on clean glass substrates with pre-patterned platinum electrodes. Glass substrates were cleaned via sonication in acetone followed by rinsing in de-ionized water. Polymer films were spin cast at 1000 RPM for 45 seconds to produce films 100-200 nm thick, which covered the substrate. A section of the thin films were removed from the Pt finger electrodes to ensure direct electrical contact during measurements by using a combination of $O_2$/Ar plasma in a March Plasma RIE. FIG. 2 is a top perspective view of the sensor along with the sensor holder. The polymer (e.g., CNT/PANI) film thickness can be varied by changing the spin speed or solution concentration.

Sensitivity of the Gas Sensor.

The sensitivity of the sensor to ammonia in the ppb range of concentrations was measured using a set-up similar to that depicted in FIG. 7. The diluted in $N_2$ to 100 ppm concentration ammonia gas was injected with flow rates under 1 sccm into the stream of extra dry $N_2$ gas, flowing with the fixed rate of 1000 sccm in the quartz chamber with the sensor inside.

The potential difference of 0.1 Volts was applied to the sensor in order to detect a current variation under the influence of the ammonia gas.

The current was converted to a voltage signal by a precision current/voltage preamplifier and digitized by a Ni A/D converter.

A 50:50 blend of (1) PANI-doped by CSA in chloroform and (2) ODA functionalized CNT in chloroform, the PANT and CNT solutions each having equal concentrations, was mixed to form a solution of PANI-CSA:ODA-CNT (the "CNT/PANI solution") in chloroform. The resulting CNT/PANI solution was tested and compared with 100% PANI-doped by CSA.

PANI and PANI/CNT films were spin cast from chloroform at speeds varying from 1000-3000 RPM at the system of electrodes.

The PANI-CSA thin film samples were characterized by measuring current flow as a function of exposure to ammonia vapors in nitrogen atmosphere at room temperature at fixed applied voltage. The duration of sensor exposure to ammonia and the concentration of ammonia gas were varied.

The resistance of the sensors was measured dependently upon concentration of ammonia (in the range of 100 ppb-10 ppm).

Figure 3:
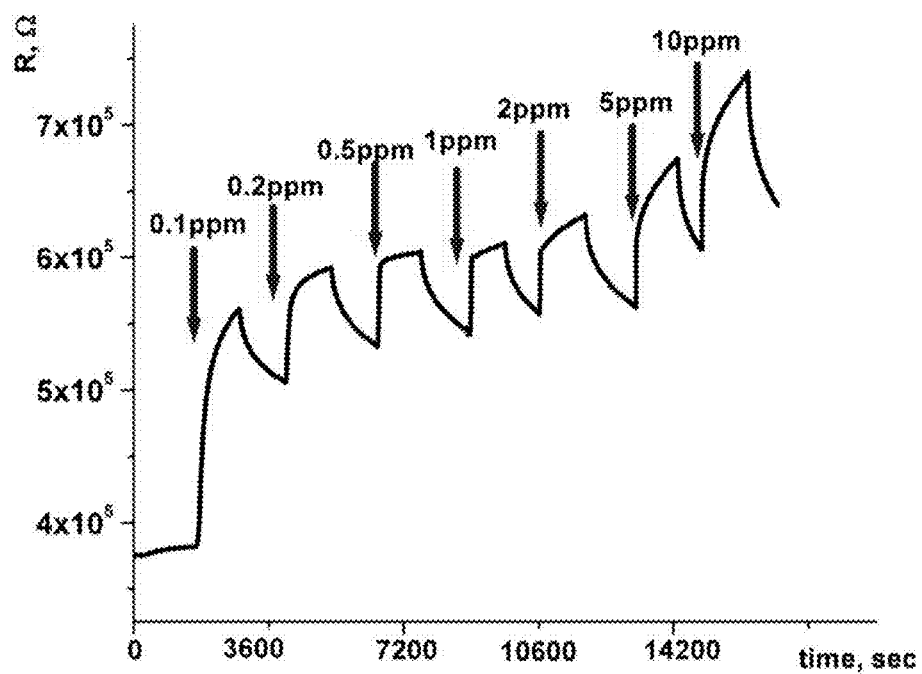
FIG. 3 is a graph showing the kinetics of the resistance of a PANI sensor.
Figure 4:
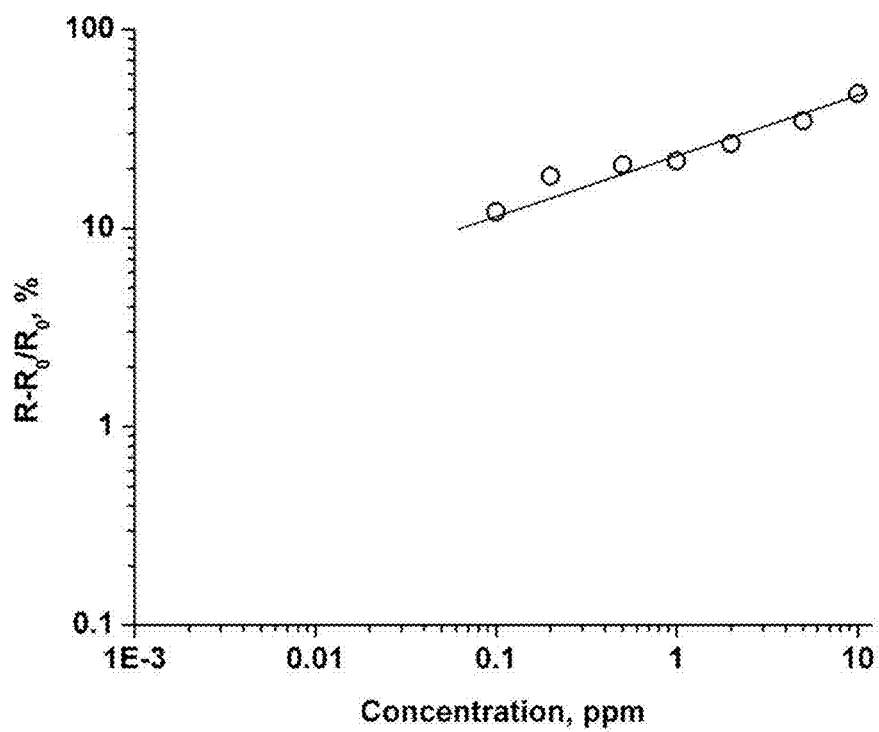
FIG. 4 is a graph showing the concentration dependence of the resistance of a PANI sensor.
Figure 5:
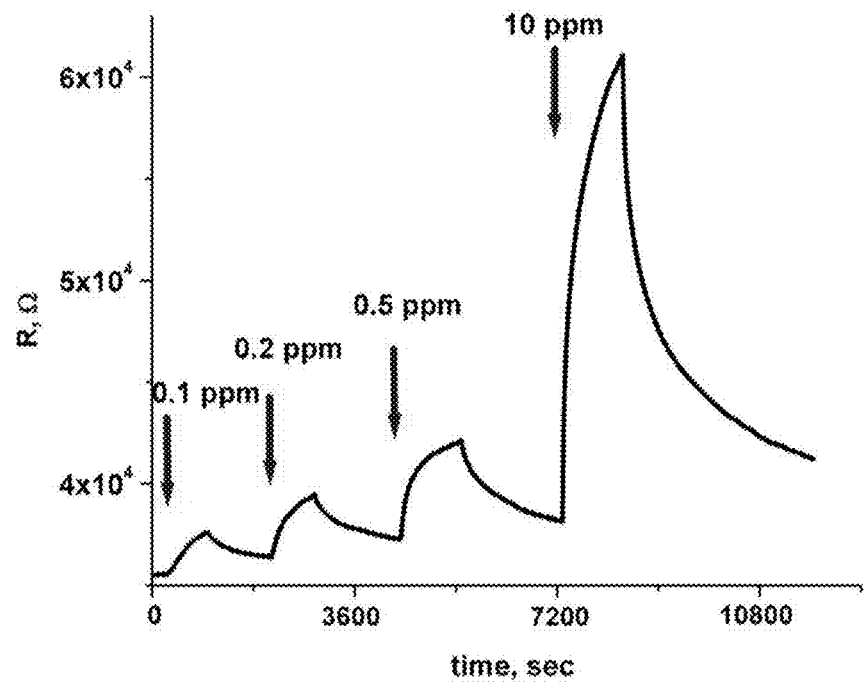
FIG. 5 is a graph showing the kinetics of the resistance of a CNT/PANI sensor according to the present invention.
Figure 6:
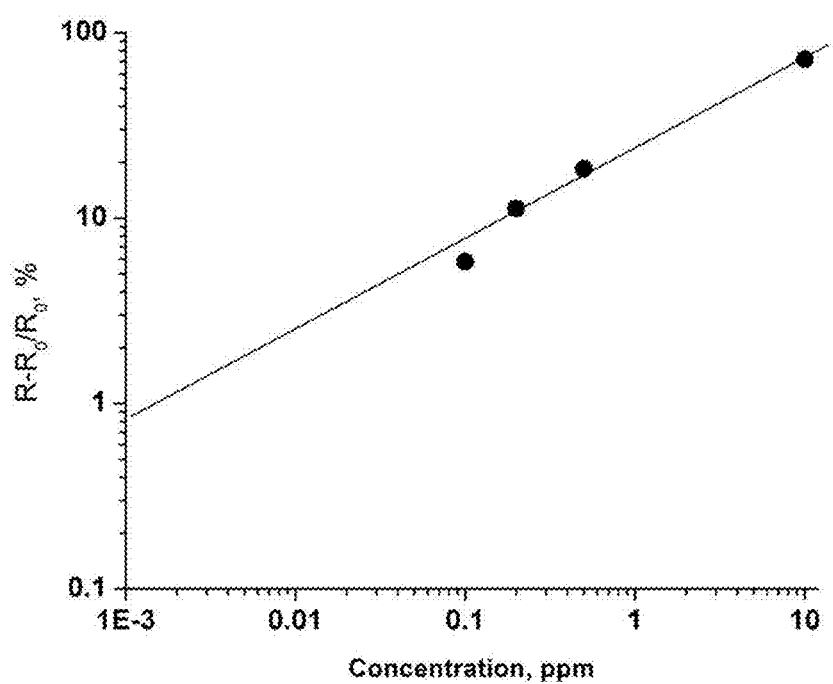
FIG. 6 is a graph showing the concentration dependence of the resistance of a CNT/PANI sensor according to the present invention.

A graph showing the kinetics of the resistance of a PANI sensor is presented in FIG. 3, and the concentration dependence of the resistance is presented in FIG. 4. A graph showing the kinetics of the resistance of the PANI-CNT (50-50%) sensor is presented in FIG. 5, and the concentration dependence of the resistance is presented in FIG. 6. The plots of FIGS. 2-6 demonstrate that the CNT-PANI nanocomposite sensors possess lower resistivity and higher sensitivity than the PANI sensor without CNTs. This is evidenced by, for example, a significant difference (in this case, one order of magnitude) in the resistance of the pure PANI sensors (~$3.7 \times 10^5$ Ohm; see baseline, FIG. 4) and the CNT/PANI sensor made according to the instant invention (~$3.6 \times 10^4$ Ohm; see baseline, FIG. 5). In certain embodiments, this high sensitivity is attributable to the thin tunneling PANI layer, and to electron transport both along the CNTs and through the PANI gaps between nanotubes. As shown in FIG. 5, in certain embodiments, sensors according to the present show reversible sensor response to even low concentrations of gaseous analyte. FIG. 5 reflects a return to the baseline even when tested at the lowest analyte concentration, 100 ppb. The figure suggests that the sensors are reversibly sensitive to even lower analyte concentrations.

Based on the lowest measured signal of 100 ppb in FIG. 5, it is estimated that sensors according to the present invention are able to detect as low as 1 ppb ammonia in gaseous environments (e.g., dry $N_2$).

While several aspects and embodiments of the present invention have been described and depicted herein, alternative aspects and embodiments may be affected by those skilled in the art to accomplish the same objectives. Accordingly, this disclosure is intended to cover all such further and alternative aspects and embodiments as fall within the true spirit and scope of the invention.

The invention claimed is:

1. An electrochemical sensor for sensing a gaseous analyte comprising:
    a substrate comprising at least two electrodes disposed thereon; and
    a carbon nanotube-polyaniline (CNT/PANI) film disposed on said substrate and in contact with at least two electrodes, wherein said CNT/PANI film comprises octadecylamine (ODA) functionalized carbon nanotubes,
    wherein said carbon nanotube-polyaniline (CNT/PANI) film comprises ODA functionalized multi-walled carbon nanotbubes coated with polyanailine doped with camphor-sulfuric acid (PANI-CSA), and
    wherein the PANI-CSA coating has an average thickness of less than 10 nm.

2. The electrochemical sensor of claim 1, wherein electron transport occurs along and/or between the ODA functionalized carbon nanotubes.

3. The electrochemical sensor of Claim 1, wherein said multi-walled carbon nanotubes have an average diameter that is greater than or equal to 10 nm and less than 50 nm.

4. The electrochemical sensor of claim 1, wherein said electrodes are platinum electrodes.

5. The electrochemical sensor of claim 1, wherein the CNT/PANI film has an average thickness of 50-100 nm.

6. The electrochemical sensor of claim 1, wherein the gaseous analyte is ammonia.

7. The electrochemical sensor of claim 6, wherein said electrochemical sensor is capable of sensing at least 1 ppb of ammonia.

8. The electrochemical sensor of claim 1, wherein the substrate comprises four to six electrodes disposed thereon.

9. The electrochemical sensor of claim 8, wherein said substrate comprises four electrodes disposed thereon.

10. The electrochemical sensor of claim 8, wherein said substrate comprises five electrodes disposed thereon.

11. The electrochemical sensor of claim 8, wherein said substrate comprises 6 electrodes disposed thereon.

12. A method for detecting ammonia in a gaseous sample, comprising:
    exposing an electrochemical sensor of claim 1 to a gaseous sample, wherein said electrochemical sensor changes resistivity in response to an amount of ammonia present in said gaseous sample;
    detecting said change in resistivity in response to ammonia in said gaseous sample by detecting a concentration of ammonia less than 200 ppb; and
    measuring the concentration of ammonia based on said change in resistivity of said electrochemical sensor.

13. The method of claim 12, wherein said exposing said electrochemical sensor to a gaseous sample comprises:
    obtaining a baseline ammonia concentration reading from said gaseous sample; and
    measuring the change in current or voltage across said electrochemical sensor, wherein the magnitude of the change in current or voltage establishes the concentration of ammonia present.

14. The method of claim 12, wherein said gaseous sample is a breath sample.

15. The method of claim 12, wherein said concentration of ammonia in said sample is less than 100 ppb.

16. The method of claim 12, wherein said concentration of ammonia in said sample is between 1 ppb and 200 ppb.

17. The method of claim 16, wherein said concentration of ammonia in said sample is about 1 ppb.

18. An electrochemical sensor for sensing a gaseous analyte comprising:
    a substrate comprising at least two electrodes disposed thereon; and a carbon nanotube-polyaniline (CNT/PANI) film disposed on said substrate and in contact with at least two electrodes, wherein said CNT/PANI film comprises octadecylamine (ODA) functionalized carbon nanotubes,
    wherein the substrate comprises four to six electrodes disposed thereon.

19. The electrochemical sensor of claim 18, wherein substrate comprises four electrodes disposed thereon.

20. The electrochemical sensor of claim 18, wherein substrate comprises five electrodes disposed thereon.

21. The electrochemical sensor of claim 18, wherein substrate comprises six electrodes disposed thereon.

22. A method for detecting ammonia in a gaseous sample, comprising:
    exposing an electrochemical sensor to a gaseous sample, the electrochemical sensor comprising a substrate comprising at least two electrodes disposed thereon, and a carbon nanotube-polyaniline (CNT/PANI) film disposed on said substrate and in contact with at least two electrodes, wherein said CNT/PANI film comprises octadecylamine (ODA) functionalized carbon nanotube, and wherein said electrochemical sensor changes resistivity in response to an amount of ammonia present in said gaseous sample;
    detecting said change in resistivity in response to ammonia in said gaseous sample by detecting a concentration of ammonia less than 200 ppb; and
    measuring the concentration of ammonia based on said change in resistivity of said electrochemical sensor, and wherein said concentration of ammonia in said sample is about 1 ppb.

23. The method of claim 22, wherein said gaseous sample is a breath sample.

* * * * *